(12) United States Patent
McDermott et al.

(10) Patent No.: US 12,133,947 B2
(45) Date of Patent: Nov. 5, 2024

(54) CATHETER ASSEMBLY INCLUDING CATHETER BODY PORTIONS WITH MODIFIABLE LENGTHS

(71) Applicant: MOZARC MEDICAL US LLC, Minneapolis, MN (US)

(72) Inventors: Sean A. McDermott, Weymouth, MA (US); Stephen W. Murray, Attleboro, MA (US)

(73) Assignee: MOZARC MEDICAL US LLC, Minneapolis, MN (US)

( * ) Notice: Subject to any disclaimer, the term of this patent is extended or adjusted under 35 U.S.C. 154(b) by 241 days.

(21) Appl. No.: 17/370,481

(22) Filed: Jul. 8, 2021

(65) Prior Publication Data

US 2023/0010361 A1 Jan. 12, 2023

(51) Int. Cl.
*A61M 1/28* (2006.01)
*A61M 25/00* (2006.01)
*A61M 25/04* (2006.01)
*A61M 39/12* (2006.01)

(52) U.S. Cl.
CPC ........ *A61M 1/285* (2013.01); *A61M 25/0009* (2013.01); *A61M 25/0026* (2013.01); *A61M 25/04* (2013.01); *A61M 39/12* (2013.01)

(58) Field of Classification Search
CPC .......... A61M 2025/0008; A61M 25/04; A61M 39/12; A61M 1/285; A61M 2039/0276; A61M 25/0009; A61M 25/0041; A61M 2025/0293; A61M 2039/0261; A61M 2039/0273; A61M 25/0026; A61M 25/02; A61M 39/0247
See application file for complete search history.

(56) References Cited

U.S. PATENT DOCUMENTS

| | | | | |
|---|---|---|---|---|
| 4,935,004 A | * | 6/1990 | Cruz | A61M 1/285 604/530 |
| 7,811,257 B2 | | 10/2010 | Saab | |
| 9,669,190 B2 | | 6/2017 | Ryan et al. | |
| 2004/0236314 A1 | * | 11/2004 | Saab | A61M 39/0247 604/539 |

(Continued)

OTHER PUBLICATIONS

Obinwa et al., "Peritoneal Dialysis Catheters," Sep. 7, 2016, 17 pages.

(Continued)

*Primary Examiner* — Brandy S Lee (57) ABSTRACT

An example catheter assembly includes a first catheter body portion defining a first lumen and a plurality of sidewall openings open to the lumen and configured to at least one of introduce fluid into a patient or remove fluid from the patient. The catheter assembly further includes a second catheter body portion defining a second lumen, a first cuff proximal to a distal end of the first catheter body portion, a second cuff distal to a proximal end of the second catheter body portion, and a connector configured to mechanically connect the first and second catheter body portions between the first and second cuffs and to fluidically connect the first and second lumens. A distance between the first and second cuffs is modifiable by at least modifying one of a length of the first catheter body portion or a length of the second catheter body portion.

19 Claims, 5 Drawing Sheets

(56) References Cited

U.S. PATENT DOCUMENTS

2015/0119922 A1* 4/2015 Kamel ................ A61M 25/104
606/194

OTHER PUBLICATIONS

Kache, et al., "Techniques for Peritoneal Catheter Placement," Aug. 1, 2018, 10 pages.
Su, Zhen, "Peritoneal Dialysis Catheter Placement and Management," Jun. 19, 2013, 16 pages.
Azura Vascular Care, "What You Should Know About Peritoneal Dialysis Catheter Placement," May 24, 2019, 11 pages.
Argyle Peritoneal Dialysis Catheters Product Catalog, downloaded on Jun. 22, 2021, from https://www.medtronic.com/content/dam/covidien/library/US/en/product/dialysis-vascular-access/argyle-peritoneal-dialysis-catheters-product-catalog.pdf, 28 pages.
U.S. Appl. No. 17/354,744, filed Jun. 22, 2021, naming inventors McDermott, et al.

* cited by examiner

CATHETER ASSEMBLY INCLUDING CATHETER BODY PORTIONS WITH MODIFIABLE LENGTHS

TECHNICAL FIELD

The present disclosure relates to medical catheters.

BACKGROUND

A medical catheter defining at least one lumen may be used with various medical procedures. For example, a medical catheter may be used for dialysis, such as peritoneal dialysis (PD). During PD, dialysate is delivered through a catheter into a peritoneal cavity of a patient. The peritoneum of the patient acts as a membrane through which waste products are removed from the blood of the patient via osmosis and diffusion. Waste products and fluid pass from the blood of the patient, through the peritoneum, and into the dialysate. After a dwell period, the PD cycler removes an effluent fluid from the peritoneal cavity, which includes the dialysate and filtered waste products, through the catheter.

SUMMARY

In examples described herein, a catheter includes a first (distal) portion, a second (proximal) portion, and a connector configured to join the first and second portions. The lengths of the first and second catheter portions are configured to be customizable by a user (e.g., a clinician, a patient, or a patient caretaker), e.g., during a medical procedure in which the catheter is introduced into a body of the patient, to enable the user to select the overall length of the catheter and/or to select a length of a subcutaneous tunnel, e.g., the distance between entry and exit points of the patient for the catheter.

In some examples, the catheter is a peritoneal dialysis catheter. In some cases, customizing the overall length of the catheter and/or the length of the subcutaneous tunnel may facilitate better peritoneal dialysis outcomes for the patient by at least enabling the catheter to be better fitted to the anatomy of the particular patient. For example, a customizable overall catheter length and subcutaneous tunnel distance allows a clinician more freedom to select a patient-specific internal peritoneal cavity entry site and a patient-specific exit site, e.g., avoiding skin folds or other patient-specific features while still allowing a distal portion of the catheter to be positioned correctly such that the catheter openings efficiently introduce or remove fluid from the peritoneal cavity of the patient, and which can impact patient comfort as well.

In some example techniques, a user determines a first cuff position on the first portion of the catheter and a second cuff position on the second portion of the catheter. The user may alter the length of one or both of the first and second portions of the catheter based on the determined cuff positions, e.g., via trimming an end of one or both catheter portions. The user may then connect the first and second portions of the catheter with a connector, such as a barbed connector configured to mechanically hold the joined ends of the catheter portions, fluidically connect the lumens of the first and second catheter portions, and seal the first and second catheter portions from leaking from the joined ends.

Clause 1: A catheter assembly includes a first catheter body portion defining a first lumen and a plurality of sidewall openings open to the lumen and configured to at least one of introduce fluid into a patient or remove fluid from the patient; a second catheter body portion defining a second lumen; a first cuff proximal to a distal end of the first catheter body portion; a second cuff distal to a proximal end of the second catheter body portion; and a connector configured to mechanically connect the first and second catheter body portions between the first and second cuffs and to fluidically connect the first and second lumens, wherein a distance between the first and second cuffs is modifiable by at least modifying one of a length of the first catheter body portion or a length of the second catheter body portion.

Clause 2: The catheter assembly of clause 1, wherein at least one of the first catheter body portion or the second catheter body portion comprises one or more markings along a length of the respective catheter body portion, wherein the one or more markings indicate a plurality of different catheter body portion lengths.

Clause 3: The catheter assembly of clauses 1 or 2, wherein at least a distal portion of the first catheter body portion is coiled.

Clause 4: The catheter assembly of any one of clauses 1 through 3, wherein the distance between the first and second cuffs is based on a determined length between a subcutaneous cuff position and a deep cuff position of the patient and based on a determined length between a pelvic gutter and the deep cuff position of the patient.

Clause 5: The catheter assembly of clause 4, wherein the deep cuff position is based on an internal peritoneal cavity entry site of the patient and the subcutaneous cuff position is based on an external exit site of the patient.

Clause 6: The catheter assembly of any one of clauses 1 through 5, wherein the connector comprises one of the first cuff or the second cuffs.

Clause 7: The catheter assembly of clause 6, wherein the one of the first cuff or the second cuff comprises at least one of a bead cuff or a disc cuff.

Clause 8: The catheter assembly of any one of clauses 1 through 7, wherein the connector comprises a body and a plurality of barbs extending from the body.

Clause 9: The catheter assembly of any one of clauses 1 through 8, wherein the connector is configured to be received in the first and second lumens to connect the first and second catheter body portions.

Clause 10: The catheter assembly of clause 9, wherein when the connector is received in the first and second lumens and connect the first and second catheter body portions, at least part of the connector remains exposed.

Clause 11: The catheter assembly of any one of clauses 1 through 10, wherein the connector is configured to be positioned external to the first and second catheter body portions to connect the first and second catheter body portions.

Clause 12: A catheter assembly includes a first catheter body portion defining a first lumen and a plurality of sidewall openings open to the lumen and configured to at least one of introduce fluid into a patient or remove fluid from the patient, wherein the first catheter body portion includes a first cuff and one or more markings along its length; a second catheter body portion defining a second lumen and comprising a second cuff and one or more markings along its length; and a connector configured to be received in the first and second lumens to mechanically connect the first and second catheter body portions between the first and second cuffs and to fluidically connect the first and second lumens, wherein a distance between first and second cuffs is modifiable by at least modifying one of a length of the first catheter body portion or a length of the second catheter body portion.

Clause 13: The catheter assembly of clause 12, wherein the distance between the first and second cuffs is based on a determined length between a subcutaneous cuff position and a deep cuff position of the patient and based on a determined length between a pelvic gutter and the deep cuff position of the patient.

Clause 14: The catheter assembly of clause 12 or 13, wherein the connector is configured to be received in the first and second lumens to connect the first and second catheter body portions.

Clause 15: The catheter assembly of clause 14, wherein when the connector is received in the first and second lumens and connect the first and second catheter body portions, at least part of the connector remains exposed.

Clause 16: The catheter assembly of clause 14 or 15, wherein the connector comprises a body and a plurality of barbs extending from the body, the plurality of barbs being configured to engage at least an inner surface of the first and second catheter body portions to secure the connector to the first and second catheter body portions.

Clause 17: The catheter assembly of any one of clauses 12 through 16, wherein the connector is configured to be positioned external to the first and second catheter body portions to connect the first and second catheter body portions.

Clause 18: A method of forming a peritoneal dialysis (PD) catheter includes determining a first cuff position on a first catheter body portion; determining a second cuff position on a second catheter body portion; modifying at least one of a length of the first catheter body portion or a length of the second catheter body portion based on the first cuff position and the second cuff position; and connecting, via a connector, the first catheter body portion and the second catheter body portion between the first cuff position and the second cuff position, wherein connecting the first and second catheter body portions comprises fluidically connecting a first lumen defined by the first catheter body portion and a second lumen defined by the second catheter body portion.

Clause 19: The method of clause 18, wherein the connector comprises a body and a plurality of barbs extending radially outwards from the body.

Clause 20: The method of clause 18 or 19, wherein the first cuff position is an internal peritoneal cavity entry site of the patient, wherein the first catheter body portion further comprises a deep cuff at the first cuff position, wherein the connector further comprises the deep cuff.

The details of one or more examples are set forth in the accompanying drawings and the description below. Other features, objects, and advantages will be apparent from the description and drawings, and from the claims.

DETAILED DESCRIPTION

The present disclosure describes medical catheters including connectors, assemblies, and techniques for making and using the medical catheter. In some examples, a connector is configured to connect first and second portions of a medical catheter (also referred to as a catheter herein) such that the first and second portions have customizable lengths.

Some catheters, such as dialysis catheters, include one or more cuffs to promote tissue in-growth and stability, e.g., for chronic applications of a catheter. In existing catheters, cuffs are attached to the catheter at the manufacturing site in a fixed position. The cuff(s) may be fixed in position such that the distance between a cuff and the distal end of the catheter is fixed and/or non-variable. In addition, if the catheter includes multiple cuffs, the cuffs being preattached to the catheter at the manufacturing site results in the distance between cuffs being fixed and/or non-variable. Both fixing the distance between a cuff and the distal end of the catheter and fixing the distance between multiple cuffs (if present) may make positioning of the distal end of the catheter in a patient more difficult and may make positioning of multiple cuffs in the patient more difficult.

Peritoneal dialysis (PD) catheters are used to access the peritoneal cavity of a patient to fill the peritoneal cavity with dialysate and to drain the dialysate. It may be desirable to position the PD catheter such that the distal end is within or near the pelvic gutter. If the distal end is too far down, the one or more sidewall openings near or at the distal end of the catheter may become plugged and may lead to patient discomfort, e.g., "drain pain." If the distal end of the catheter is not far down enough into the peritoneal cavity, then the exchange of fluid and/or dialysate may not be able to be completed during a dialysis session. Further, there may be constraints on the exit and entry points of a patient for the catheter. For example, different patients have differing thicknesses of skin, fat, and other tissue, and a fixed distance between a subcutaneous cuff of the PD catheter and a peritoneal wall cuff of the PD catheter may make it more difficult to find suitable exit/entry points on a particular patient.

The present disclosure describes a catheter configured to enable a user (referred to herein generally as a clinician) to select the position of one or more cuffs along the longitudinal length of the catheter by changing the length of the catheter between at least two cuffs. The catheter includes a first (distal) portion, a second (proximal) portion, and a connector configured to join the first and second portions. The lengths of the first and second catheter portions are configured to be customizable by a user/clinician to enable the user to select the overall length of the catheter and/or to select a length of a subcutaneous tunnel, e.g., to accommodate different patient anatomies or clinician preferences.

For example, a user may determine one or more desired internal peritoneal cavity entry sites and one or more patient exit sites. The user may then determine a desired subcutaneous tunnel length based on the one or more desired internal peritoneal cavity entry sites and one or more patient exit sites. The subcutaneous tunnel extends between an internal peritoneal cavity entry site and a respective patient exit site. The user may then determine a first cuff position on the first portion of the catheter and a second cuff position on the second portion of the catheter. The user may then alter the length of one or both of the first and second portions of the catheter based on the determined cuff positions and the determined subcutaneous tunnel length, e.g., via trimming an end of one or both catheter portions. The user may then connect the first and second portions of the catheter with a connector, such as a barbed connector configured to mechanically hold the joined ends of the catheter portions, fluidically connect the lumens of the first and second catheter portions, and substantially fluidically seal the joint between the first and second catheter portions to help prevent leaking from the joined ends (e.g., completely prevent the ingress or egress of fluids through the joint or prevent a physiologically significant amount of fluid from exiting or entering the catheter through the joint).

Figure 1:
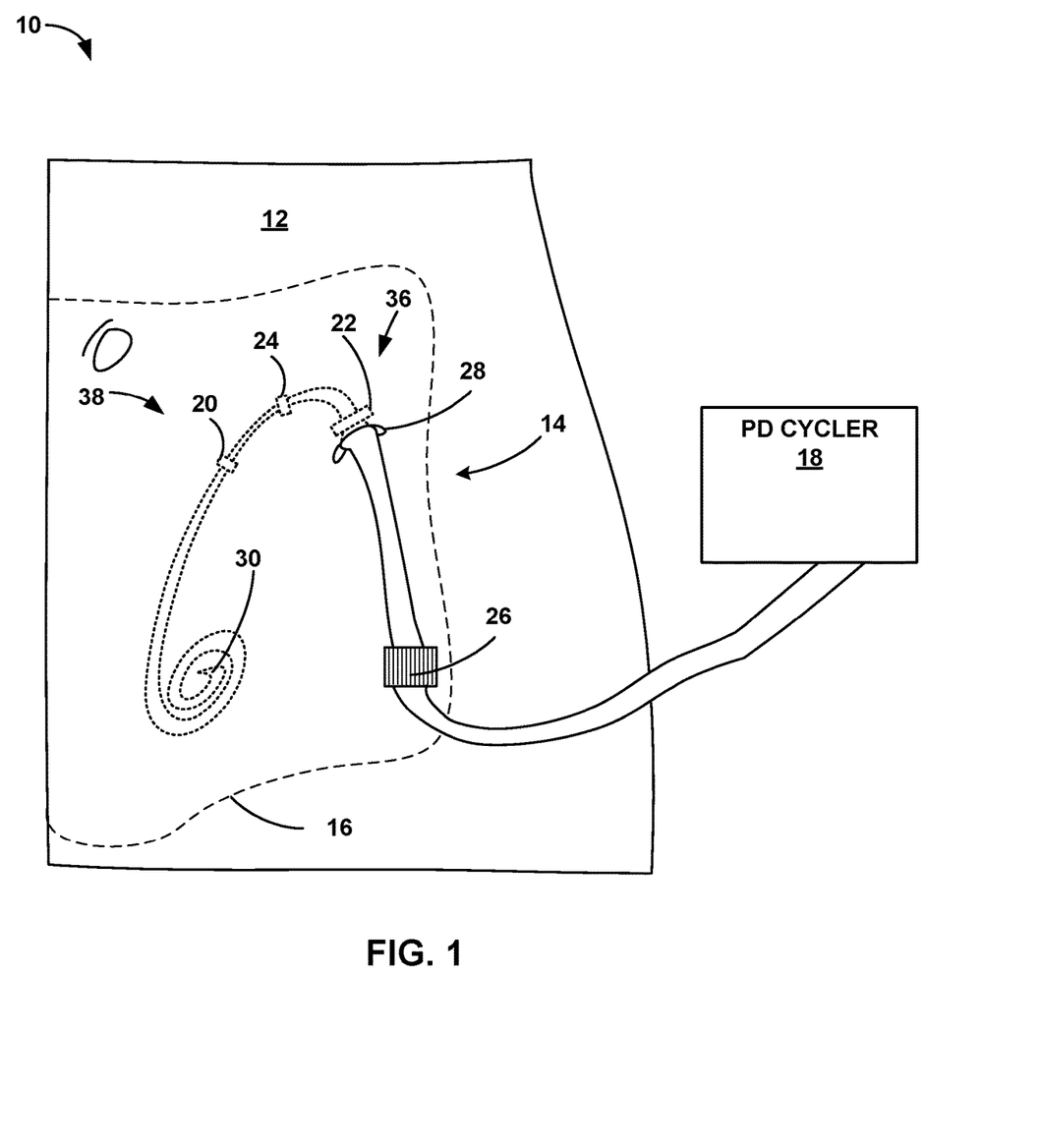
FIG. 1 is a diagram illustrating an example PD system configured to provide a patient with PD treatment.

FIG. 1 is a diagram illustrating an example PD system 10 configured to provide a patient 12 with PD treatment. PD system 10 includes a catheter 14, cuffs 20, 22, connector 24, and a PD cycler 18. Catheter 14 is illustrated in FIG. 1 as extending into a peritoneal cavity 16 of patient 12. Patient 12 ordinarily will be a human patient. In some cases, however, PD system 10 may be applied to other mammalian or non-mammalian, non-human patients.

PD cycler 18 is configured to deliver a dialysate into peritoneal cavity 16 via catheter 14. The dialysate remains in peritoneal cavity 16 for a dwell period, which has a duration sufficient for the exchange of waste products across a peritoneum of patient 12 to take place. In some such examples, PD cycler 18 may be disconnected from catheter 14 during the dwell period. In other examples, however, PD cycler 18 remains connected to catheter 14 during the dwell period. After the dwell period, PD cycler 18 removes fluid from peritoneal cavity 16. The fluid drained from peritoneal cavity 16 can be referred to as an effluent fluid, which contains the dialysate and the waste products removed from the blood of patient 12.

In some examples, the waste products may be removed by the dialysate due to a concentration gradient, e.g., due to the concentration of an osmotic agent in the dialysate, created in peritoneal cavity 16 when peritoneal cavity 16 is filled with the dialysate, which drives ultrafiltration and convective solute removal. The dialysate may include water, and dextrose or other sugars, salt, electrolytes, ions, and/or minerals as the osmotic agent. In some examples, the dialysate is dextrose-based, e.g., includes dextrose as the osmotic agent.

In order to deliver the dialysate into peritoneal cavity 16 and remove the effluent fluid from peritoneal cavity 16, PD cycler 18 is connected to catheter 14, such as via an adapter 26, which provides the necessary mechanical connection between catheter 14 and PD cycler 18 to establish fluid communication therebetween. Catheter 14 may be any fluid delivery conduit capable of being inserted into peritoneal cavity 16 and connected to PD cycler 18 to facilitate PD treatment of patient 12. Catheter 14 may be inserted into patient 12 via an exit site 28, and be configured to remain in patient 12 on a long-term basis, with a portion of catheter 14 remaining within peritoneal cavity 16 and a portion of catheter 14 residing outside of patient 12.

Catheter 14 have any suitable configuration. For example, the portion of catheter 14 that remains within peritoneal cavity 16 may be straight or curvilinear, such as pig-tailed (e.g., coiled). In some examples, a distal portion of catheter 14 has a swan neck (e.g., a curved portion up to about 180 degrees), which may help position catheter 14 at exit site 28 as intended. Catheter 14 has any suitable length for accommodating PD treatment. For example, catheter 14 may be between about 57 cm and about 62 cm in length (e.g., from internal peritoneal cavity entry site of patient 12 such as cuff 20 as shown to a distal-most end of catheter 14 within peritoneal cavity 16), and may be between about 2.5 mm and about 3.5 mm in diameter. In other examples, other shapes, sizes (e.g., length or diameter), and/or configurations may be used. An example of catheter 14 includes, but is not limited to, Argyle™ Peritoneal Dialysis Catheter available from Medtronic, Inc. of Minneapolis, MN.

Cather 14 may include one or more cuffs. In the example shown, catheter 14 includes cuff 20 configured to be positioned along the length of catheter 14 such that cuff 20 is positioned at or near an internal peritoneal cavity entry site of patient 12 when catheter 14 is placed within patient 12, e.g., cuff 20 may be a "deep cuff." Catheter 14 also includes cuff 22 configured to be positioned along the length of catheter 14 such that cuff 20 is positioned at or near exit site 28 of patient 12, e.g., cuff 22 may be a "subcutaneous cuff."

Figures 2A, 2B:
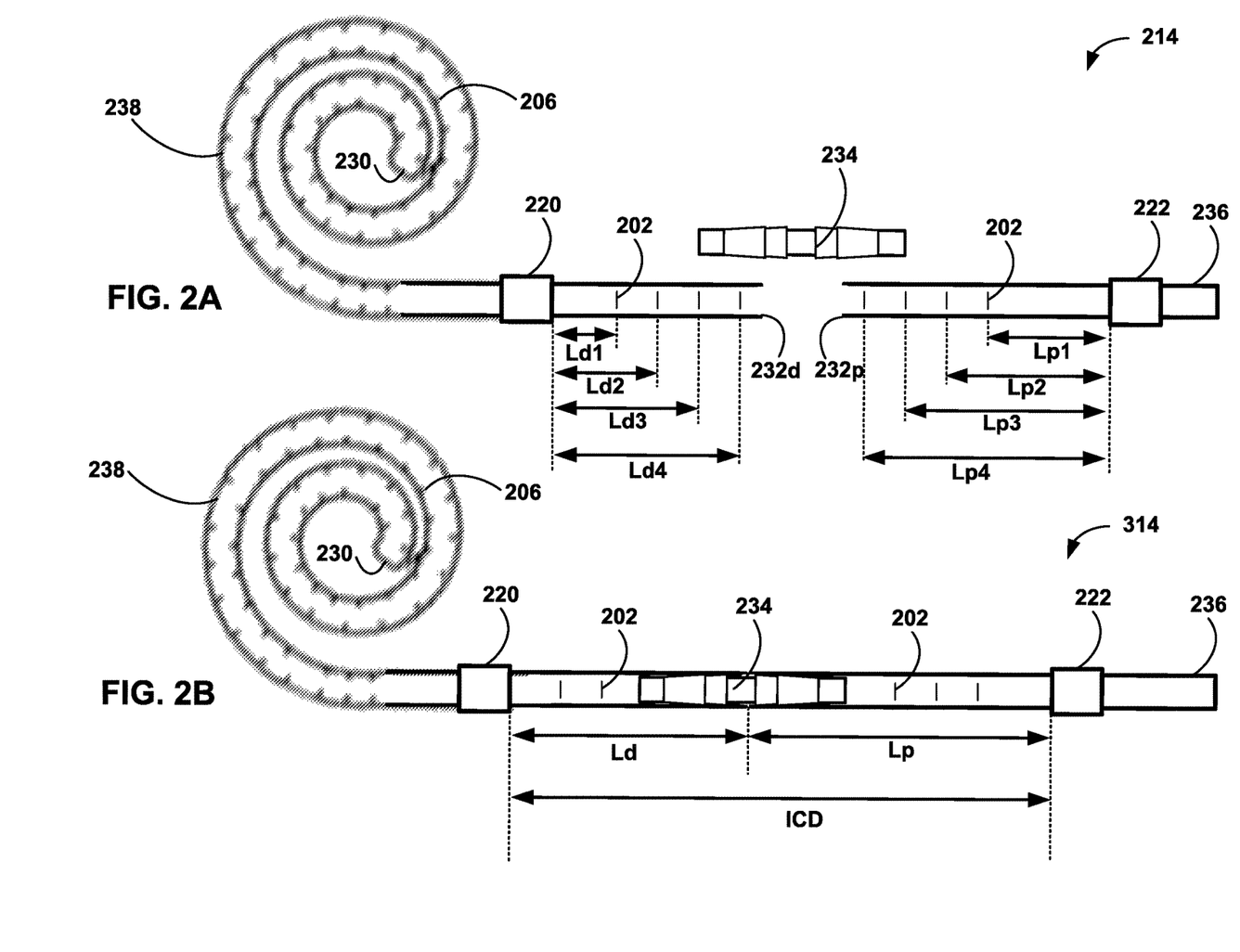
FIG. 2A is a conceptual illustration of a PD catheter including separate first and second portions and a connector.
FIG. 2B is a conceptual illustration of a PD catheter including first and second portions connected by a connector.

Catheter 14 includes two or more separate catheter body portions configured to be joined together via connector 24, e.g., prior to insertion into patient 12. For example, catheter 14 may include a distal body portion 38 and a proximal body portion 36. The distal body portion 38 defines a distal lumen portion and a plurality of sidewall openings that are open to the distal lumen portion and configured to allow fluid to pass through them, e.g., so as to introduce fluid into patient 12 (e.g., into peritoneal cavity 16) or remove fluid from the patient that is transported via the distal lumen portion. The distal body portion 38 may include cuff 20, and may have a suitable length between the distal-most end of the distal body portion 38 and cuff 20, e.g., about 57 cm and about 62 cm. The distal body portion 38 may also include a first inter-cuff length, e.g., a distal body portion inter-cuff length that extends from cuff 20 in a direction opposite the distal-most end 30 of the distal body portion 38, such as distal inter-cuff length Ld between cuff 20 (e.g., a proximal end of cuff 20, a distal end of cuff 20, or a midpoint of cuff 20) and distal body portion 38 inter-cuff end 232d as illustrated in FIG. 2B.

The proximal body portion 36 defines a proximal lumen portion configured to transport fluid. The proximal body portion 36 may include cuff 22, and may be configured to attach to adapter 26 or otherwise exit patient 12 via exit site 28. The proximal body portion 36 may also include a second inter-cuff length, e.g., a proximal body portion 36 inter-cuff length that extends from cuff 22 in a direction towards cuff 20 (when connected to the distal body portion), such as proximal inter-cuff length Lp between cuff 22 and proximal body portion 36 inter-cuff end 232p as illustrated in FIG. 2B.

In some examples, at least one of the distal and/or proximal inter-cuff lengths of the distal or proximal body portions 38, 36, respectively, may be configured to be modified by a user. For example, a user may determine a desired distance between cuff 20 and cuff 22, e.g., a subcutaneous tunnel length, and the user may modify one or both of the distal/proximal inter-cuff lengths via cutting, or trimming, the distal and/or proximal body portions 38, 36 such that the distal/proximal inter-cuff lengths, once joined together, are substantially equal to the desired subcutaneous tunnel length. In some examples, to facilitate positive PD therapy outcomes, a clinician may determine a desired subcutaneous tunnel length based on patient 12 anatomy, e.g., based on a desired exit site 28 that may avoid folds or other anatomical features of patient 12. In some examples, the user may determine one or more desired internal peritoneal cavity entry sites and one or more desired exit sites of patient 12, and may determine the desired subcutaneous tunnel length based on the one or more entry/exit sites. The user may then customize and/or modify the length of catheter 14 between cuff 20 and cuff 22 by modifying the length of one or both of the distal/proximal inter-cuff lengths, e.g., via trimming, such that the inter-cuff distance between cuff 20 and cuff 22 is substantially equal to the desired subcutaneous tunnel length. The user may then join the distal body portion 38 and the proximal body portion 36 with connector 24.

Connector 24 is configured to mechanically connect and/or hold the joined ends of the distal body portion 38 and the proximal body portion 36 of catheter 14. Connector 24 is configured to fluidically connect the distal lumen portion and the proximal lumen portion of the distal and proximal body portions 38, 36, e.g., to form a continuous lumen of catheter 14 configured to transport fluid. Connector 24 may be configured to seat the joined ends of the distal and proximal lumen portions, e.g., to reduce and/or prevent fluid from leaking from the joined ends of the distal and proximal body portions 38, 36. In some examples, connector 24 may be barbed, e.g., so as to both mechanically connect the joined ends together and to press into inner surface of the distal and proximal lumen portions to form a seal within the distal and proximal lumen portions. In some examples, connector 24 may be smooth and may mechanically connect the joined ends together and seal the distal and proximal lumen portions. Connector 24 may define a connector lumen configured to transport fluid. In some examples, catheter 14 may define multiple lumens, and connector 24 may be configured to fluidically connect each lumen of the distal lumen portion to the corresponding lumen of the proximal lumen portion of distal and proximal body portions 38, 36.

In some examples, to mechanically and fluidically connect the distal and proximal body portions of catheter 14, connector 24 is configured to be received in the distal lumen portion and/or the proximal lumen portion of the distal and proximal body portions, respectively, e.g., by friction fit or interference fit. That is, connector 24 may be positioned radially inward of the outer surface of catheter 14 when connector 24 functions to join the proximal and distal body portions 36, 38. In these examples, connector 24 may be entirely contained within a lumen of catheter 14 or may be partially exposed to an environment outside of catheter 14. In other examples, to mechanically and fluidically connect the distal and proximal body portions 38, 36 of catheter 14, connector 24 is configured to be positioned radially outward of the distal lumen portion and/or the proximal lumen portion. For example, connector 24 may be positioned on an outer surface of catheter 14.

In some examples, connector 24 may be made of at least one of stainless steel, titanium, a metal, a plastic and/or polymer, or any suitable material configured to mechanically and fluidically connect, and seal, the distal and proximal body portions 38, 36 of catheter 14. In some examples, connector 24 may replace cuff 20 or cuff 22. For example, connector 24 may include a Dacron™ cuff, a bead cuff, a disc cuff, or a bead-and-flange such that when connecting the distal and proximal body portions 38, 36 of the catheter 14, the cuff, bead, disc, and/or bead-and-flange of connector 24 is exposed to patient tissue and performs the functions of cuff 20, e.g., to anchor catheter 14 at or near the internal peritoneal cavity entry site and/or seal the internal peritoneal cavity entry site via promotion of tissue growth. In examples in which connector 24 may be both connector and deep cuff (e.g., cuff 20), the distal body portion 38 may not include a cuff 20 and/or the user may modify the length of the distal body portion 38 at any position along its length, e.g., the user may cut or trim off a length of the distal body portion 38 including cuff 20.

Cuffs 20, 22 may be configured to promote and/or encourage growth of tissue, collagen, or epidermal tissue on, around, or within each of cuffs 20, 22, e.g., cuffs 20, 22 may include a cuff body material configured to promote and/or encourage growth of tissue, collagen, or epidermal tissue on, around, or within cuffs 20, 22. In some examples, cuffs 20, 22 may comprise a biocompatible porous material, such as a polyester fabric, Dacron™, and the like. In some examples, cuffs 20, 22 may include an antimicrobial coating, e.g., the cuff body material may include an antimicrobial coating.

Cuffs 20, 22 may have any suitable width, where the width is measured in a direction orthogonal to the direction in which the length is measured. In some examples, cuffs 20, 22 may have a width that is less than the length between exit site 28 and or an internal peritoneal cavity entry site of patient 12.

FIG. 2A is a conceptual illustration of an example PD catheter 214 including a distal body portion 238 physically separated from a proximal body portion 236 and a connector 234. PD catheter 214 is an example of catheter 14 of FIG. 1. FIG. 2B is a conceptual illustration of a PD catheter including distal body portion 238 and proximal body portion 236 mechanically and fluidically connected by connector 234.

In the examples shown in FIGS. 2A and 2B, distal body portion 238 includes a coiled (e.g., pigtailed) shape configured to be positioned within peritoneal cavity 16 when catheter 214 is used to provide patient 12 with PD. Distal body portion 238 further includes a plurality of sidewall openings 206 along at least a portion of the length of distal body portion 238. The one or more sidewall openings 206 are configured to introduce fluid from a lumen of the respective catheter into peritoneal cavity 16 of patient 12 or remove fluid from peritoneal cavity 16, or both. Distal body portion 238 also includes cuff 220, which may be a deep cuff and is an example of cuff 20 of FIG. 1. Proximal body portion 236 includes cuff 222, which may be a subcutaneous cuff and is an example of cuff 22 of FIG. 1.

In the examples shown, catheter 214 includes one or more markings 202 along a length of both distal body portion 238 and proximal body portion 236. Markings 202 indicate a plurality of different distal body portion 238 inter-cuff lengths Ld1-Ld4 selectable by a clinician (or other user) and a plurality of different proximal body portion 236 inter-cuff lengths Lp1-Lp4 selectable by the clinician. Markings 202 may be visual guides for selecting and modifying the inter-cuff length Ld of the distal body portion and the inter-cuff length Lp of the proximal body portion, e.g., so as to customize the inter-cuff distance ICD between cuffs 220, 222 when catheter 214 is assembled together via connector 234. In some examples, markings 202 may be configured to guide a clinician as to where modify the length of distal and/or proximal body portions 238, 236, and the clinician may select a length corresponding exactly to one of markings 202 or may select a length that is between markings 202. In some examples, markings 202 may be regularly spaced and/or irregularly spaced, and may be close enough to provide enough resolution in order to select and modify a length of the distal and/or proximal body portions 238, 236 with adequate resolution, e.g., to within 10 mm, 1 mm, 0.1 mm, or any suitable length resolution. Markings 202 may be any type of marking, e.g., printed, recesses, bumps, stickers, or any suitable marking type visible to or otherwise perceivable by a user.

For example, a clinician may determine a desired inter-cuff distance for PD catheter 214 based on patient 12 anatomy. The clinician may then use markings 202 as guides to select a distal inter-cuff lengths, e.g., the clinician may select Ld4 and Lp4, and may modify the inter-cuff lengths of the distal and proximal body portions 238, 236 based on Ld4 and Lp4, such as by cutting along the line corresponding to Ld4 and Lp4. The clinician may then connect distal body portion 238 and proximal body portion 236 via connector 234. In some examples, the clinician may connect distal body portion 238 and proximal body portion 236 by at least press fitting the ends of distal body portion 238 and proximal body portion 236 between cuffs 220, 222 over connector 234, resulting in catheter 214 with inter-cuff distance ICD=Ld+Lp as illustrated in FIG. 2B. In the example shown in FIG. 2B, Ld and Lp may be any inter-cuff distance selected by the clinician, e.g., any of Ld1-Ld4 and Lp1-Lp4, in any combination. For example, the clinician may independently adjust the length of the distal body portion 238 from proximal body portion 236 by selecting any suitable Ld and Lp lengths. The clinician may cut along markings 202 or cut between the markings 202 to achieve the desired length of distal body portions 238.

Although the lengths shown in FIGS. 2A and 2B, including Ld1-Ld4, Lp1-Lp4, Ld, Lp, and ICD, are measured using the proximal-most end of cuff 220 or the distal-most end of cuff 222, in other examples, the lengths may be measured using other parts of cuffs 220, 222, such as the distal-most end of cuff 220, the proximal-most end of cuff 222, or the mid-point of cuffs 220, 222.

Figure 3A:
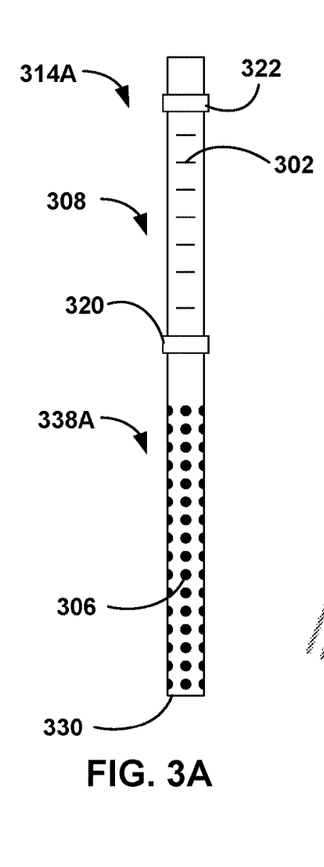
FIG. 3A is a conceptual illustration of an example straight PD catheter that may be used in the PD system of FIG. 1.
Figure 3B:
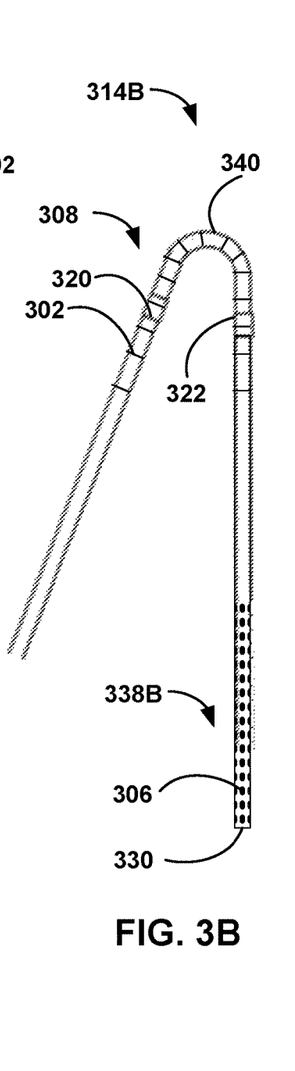
FIG. 3B is a conceptual illustration of an example swan-neck PD catheter that may be used in the PD system of FIG. 1.
Figures 3C, 3D:
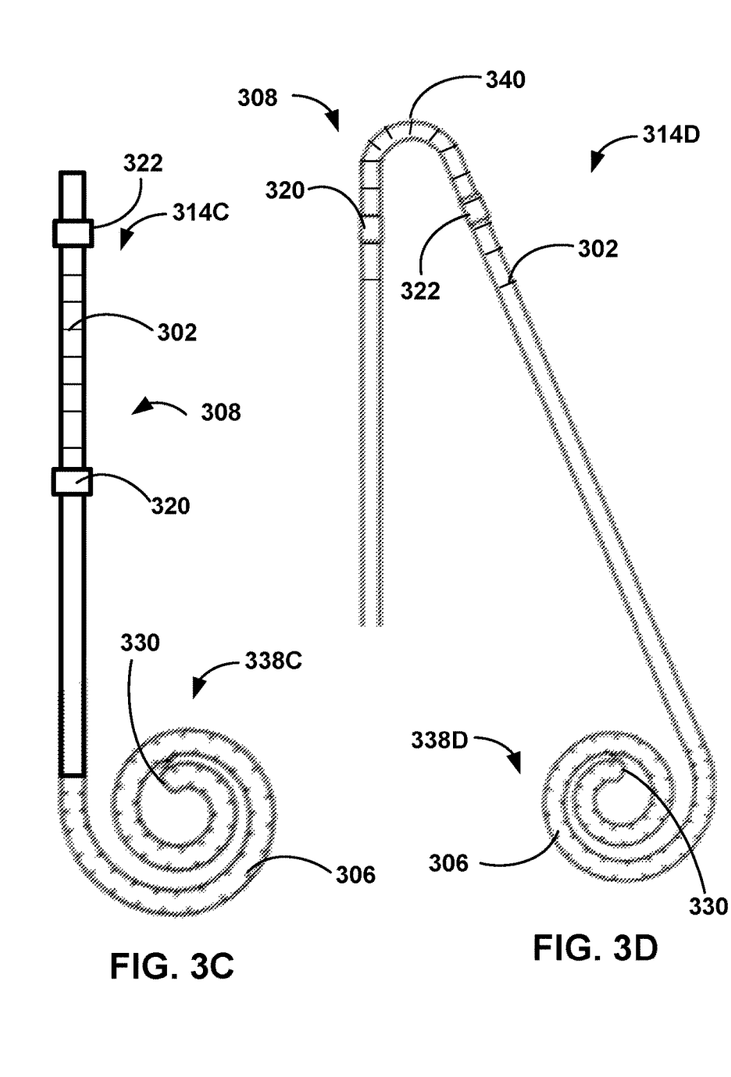
FIG. 3C is a conceptual illustration of an example straight PD catheter with a coiled intraperitoneal segment that may be used in the PD system of FIG. 1.
FIG. 3D is a conceptual illustration of an example PD swan-neck catheter with a coiled intraperitoneal segment that may be used in the PD system of FIG. 1.

FIGS. 3A-3D are conceptual illustrations of example PD catheters of differing types and which are examples of catheter 14 of FIG. 1 or catheter 214 of FIGS. 2A and 2B. FIGS. 3A-3D are described concurrently below. FIG. 3A is a conceptual illustration of an example straight (e.g., Tenckhoff) PD catheter 314A that may be used in the PD system of FIG. 1. FIG. 3B is a conceptual illustration of an example swan-neck catheter 314B that may be used in the PD system of FIG. 1. FIG. 3C is a conceptual illustration of an example catheter 314C with a coiled intraperitoneal segment that may be used in the PD system of FIG. 1. FIG. 3D is a conceptual illustration of an example swan-neck catheter 314D with a coiled intraperitoneal segment that may be used in the PD system of FIG. 1.

In the example shown in FIGS. 3A and 3B, catheters 314A and 314B include a straight distal portion 338A, 338B, respectively, that is configured to be positioned within peritoneal cavity 16 when catheter 314A, 314B is used to provide patient 12 with PD. In other examples, however, the distal portion can have another suitable shape, e.g., coiled or a different curvilinear shape. For example, catheters 314C and 314D include a coiled (e.g., pigtailed) distal portion 338C, 338D, respectively. Additionally, catheters 314B and 314D are shown to have a preformed bend 340, which may help decrease stress on exit site 28 (FIG. 1) during use of catheters 314B, 314D.

In the examples, shown, catheters 314A-314D include one or more sidewall openings 306 along at least a portion of the length of distal portions 338A-338D and towards the distal-most end 330. The one or more sidewall openings 306 are configured to introduce fluid from a lumen of the respective catheter into a peritoneal cavity of patient 12 or remove fluid from the peritoneal cavity of patient 12, or both.

In the examples shown, catheters 314A-314D are each illustrated as having connected distal and proximal portions via a connector (not visible), and each include cuffs 320, 322. Catheters 314A-314D each also include one or more markings 302 along a length of the elongated catheter body 308 of each of catheters 314A-314D. Markings 302 indicate a plurality of inter-cuff lengths selectable by a clinician (or other user). In some examples, the clinician may select a length corresponding exactly to one of markings 302 or may select a length that is between markings 302. In some examples, markings 302 may be regularly spaced and/or irregularly spaced, and may be close enough to provide enough resolution in order to select and modify a length of the distal and/or proximal body portions with adequate resolution, e.g., to within 10 mm, 1 mm, 0.1 mm, or any suitable length resolution. Markings 302 may be any type of marking, e.g., printed, recesses, bumps, stickers, or any suitable marking type visible to a user.

Figure 4:
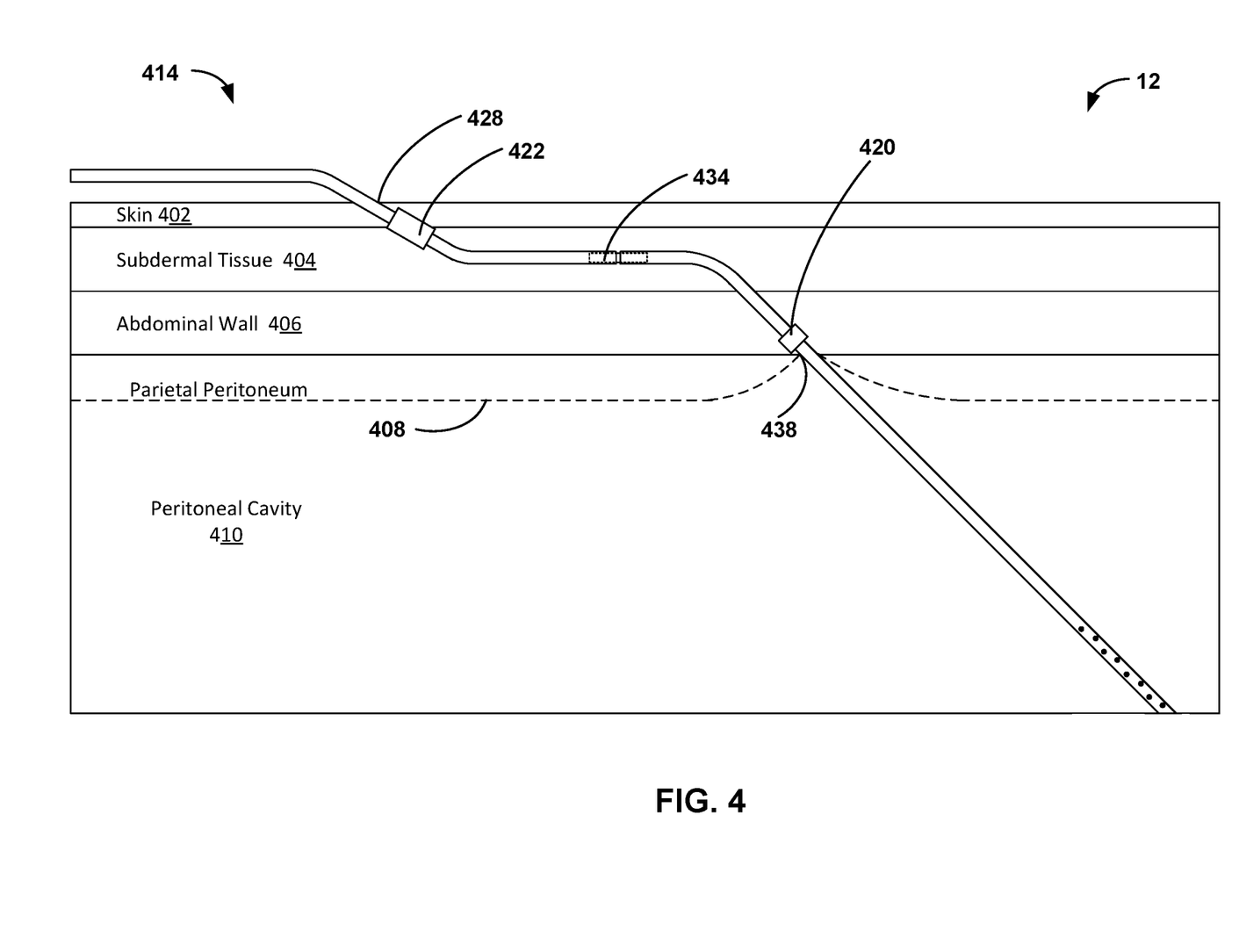
FIG. 4 is a conceptual cross-sectional view of an example placement of one or more cuffs and a connector of a PD catheter within a patient.

FIG. 4 is conceptual cross-sectional view of an example placement of PD catheter 414 and positioning of cuffs 420, 422 within a patient 12. Catheter 414 may be an example of any of catheters 14, 214, and 314A-314D of FIGS. 1-3.

In some examples, the desired inter-cuff distance between cuff 420 and cuff 422 may be based on anatomy of patient 12, where the length is measured along a longitudinal axis of catheter 414 having both distal and proximal portions connected via connector 434. For example, a clinician may determine the positions of, and the distance between, cuffs 420, 422 based on the thicknesses of skin 402, subdermal tissue 404, and the abdominal wall 406 at or near patient exit site 428 and peritoneal cavity entrance site 438, as well as a length of catheter 414 that a clinician determines should run within any and/or all of skin 402, subdermal tissue 404, and abdominal wall 406. In some examples, cuff 422 may be positioned so as to be subcutaneous and proximate to skin 402, and cuff 420 may be positioned to be a "deep" cuff and/or a peritoneal cuff at or near an inner surface of abdominal wall 406 and/or the parietal peritoneum 408.

In some examples, the clinician may select the positions of one or both cuffs 420, 422 further based on the length between cuff 420 and/or cuff 422 and the distal end of catheter 414 (not shown), e.g., which may be based on the locations of exit site 428 and/or peritoneal cavity entrance site 438 and the length and/or size of peritoneal cavity 410 of patient 12. These lengths may differ based on the anatomy of a particular patient. For example, the clinician may select the positions of cuffs 420, 422 such that sidewall openings of catheter 414 do not collapse, compress, or otherwise become obstructed to fluid flow within peritoneal cavity 410. The clinician may select the positions of cuffs 420, 422 such that the distal end of catheter 414 is not too long between peritoneal cavity entrance site 438 and the bottom of the pelvic gutter and thereby avoid and/or reduce the chance of the distal end of catheter 414 at least partially falling over within peritoneal cavity 410 causing the sidewall openings to become plugged, and resulting in drain pain. Additionally, the clinician may select the positions of cuffs 420, 422 such that the distal end of catheter 414 is not too short between peritoneal cavity entrance site 438 and the pelvic gutter to facilitate fluid removal, e.g., and avoid incomplete exchange of fluids via catheter 414.

In some examples, a user and/or clinician may determine the locations of exit site 428 and/or peritoneal cavity entrance site 438 based on patient 12 anatomy. For example, a clinician, user, and/or patient 12 may wish to avoid folds in skin 402 and/or the abdominal area of patient 12. The clinician may determine one or more desired exit sites 428, determine a length that catheter 414 should run within any and/or all of skin 402, subdermal tissue 404, and the abdominal wall 406, which may be based on a desired peritoneal cavity entrance site 438, determine a length of the distal portion of catheter 414 for adequate and/or optimal PD, e.g., such that catheter 414 is positioned correctly within peritoneal cavity 410 (e.g., so as to avoid positioning catheter 414 with a distal portion that is too long or too short within peritoneal cavity 410 of patient 12, as described above), and the position and attach cuffs 420, 422 accordingly based on those determinations.

Figure 5:
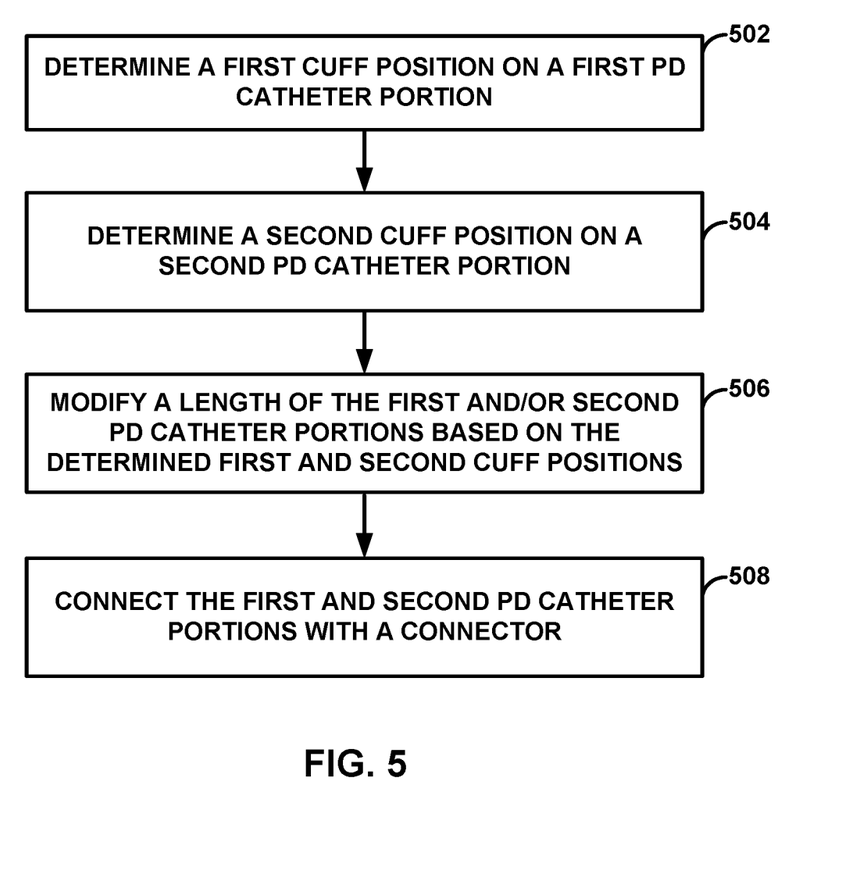
FIG. 5 is a flow diagram of an example method of attaching a cuff to a catheter.

FIG. 5 is a flow diagram of an example method of forming a catheter, such as a PD catheter. Although the example technique of FIG. 5 is described with respect to catheters 14, 214, 314A-314D, and 414 of FIGS. 1-4 and patient 12 of FIG. 4, the example technique of FIG. 5 may be performed to form any type of catheter including a modifiable length between cuffs via a connector. In some examples, the technique of FIG. 5 may be performed by any suitable user, such as a clinician.

A user may determine a first cuff position on a first PD catheter portion (502). The user may further determine a second cuff position on a second PD catheter portion (504). In some examples, a user may determine the first and second cuff positions based on a determination of the location of exit site 428, a determination of the location of peritoneal cavity entrance site 438, and/or a determination of a desired subcutaneous tunnel length, each of which may be based on the anatomy of patient 12. For example, the user may determine the first and second cuff positions and the desired subcutaneous tunnel length based on a thickness of tissue layers between a skin surface of patient 12 and the peritoneal cavity 410 (FIG. 4). For example, the user may determine a peritoneal cavity entrance site 438 based on a length of the distal portion of catheter 414 and a size of peritoneal cavity 410 (which can be an approximate or measured size). As an example, the user may select peritoneal cavity entrance site 438 such that once catheter 414 (as fully assembled and/or connected) is positioned within peritoneal cavity 410, the distal portion of catheter 414 is not kinked, bent, or otherwise positioned to block fluid flow through to sidewall openings 206 in the distal portion 238. The user may then determine a position of cuffs 420, 422 (e.g., as a deep cuff 220 and a subcutaneous cuff 222) accordingly based on that determined length.

The clinician, user, and/or patient 12 may additionally wish to avoid folds in skin 402 and/or the abdominal area of patient 12, and the user may then determine one or more desired exit sites 428 based on any patient 12 feature including avoiding skin folds. The clinician and or user may then determine a length that catheter 414 should run within any and/or all of skin 402, subdermal tissue 404, and the abdominal wall 406 between peritoneal cavity entrance site 438 and exit site 428, e.g., a subcutaneous tunnel length. The user may then determine a position of cuffs 420, 422 accordingly based on those determinations, e.g., the length of the distal portion of the catheter 414 for adequate and/or optimal PD and a determined peritoneal cavity entrance site 438 and the subcutaneous tunnel length, e.g., the length that catheter 414 should run between the determined peritoneal cavity entrance site 438 and one or more desired exit sites 428.

In some examples, the user determines only one cuff position, e.g., only subcutaneous cuff 422 position, only deep cuff 420 position 420, or any other cuff position, each of which may be based on the lengths described above and/or exit site 428 and peritoneal cavity entrance site 438 or based other criteria, e.g., which may be patient-specific. In some examples, the user may determine the position of one or more cuffs 420, 422, using markings on the catheter, such as markings 202. The user may determine the position for a cuff 220, 222 exactly on one or more marking 202, or the user may determine the position of one or more cuffs 220, 222 using markings 202 as a guide, e.g., for later modifying the length of the first PD catheter portion and/or the second PD catheter portion. In some examples, the first PD catheter portion may correspond to distal body portion 238 of FIG. 2 and the second PD catheter portion may correspond to proximal body portion 236 of FIG. 2.

The user may modify a length of the first and/or second PD catheter portions based on the determined first and second cuff positions (506). For example, the user may modify one or both of the first and second inter-cuff lengths via cutting, or trimming, the catheter portions such that the distal/proximal inter-cuff lengths, e.g., Ld and Lp of FIG. 2B, once joined together, are substantially equal to the desired subcutaneous tunnel length, e.g., inter-cuff distance ICB as illustrated in FIG. 2B.

The user may connect the first PD catheter portion and the second PD catheter portion between the first cuff position and the second cuff position with a connector (508). For example, the user may press fit at least a portion of each of the first and second PD catheter portions over opposite ends of a connector, such as any of connectors 24, 234, 434, such that the inter-cuff ends 232d, 232p of both the first and second PD catheter portions are over the connector and a first lumen defined by the first PD catheter portion is fluidically connected to a second lumen defined by the second PD catheter portion. In some examples, the user may fit at least a portion of each of the first and second PD catheter portions over opposite ends of the connector, or the user may insert at least a portion of each of the opposite ends of the connector into at least a portion of each inter-cuff end 232d, 232p of the first and second PD catheter portions such that the inter-cuff ends 232d, 232p are substantially close and/or proximal to each other and/or at least partially abut. As illustrated in FIG. 2, inter-cuff end 232d may be proximal to a distal end of distal body portion 238 and inter-cuff end 232p may be distal to a proximal end of proximal body portion 236.

In some examples, the connector may comprise a body and plurality of barbs extending radially outwards from the body. The plurality of barbs may be configured to engage at least an inner surface of first PD catheter portion and the second PD catheter portion, e.g., at least an inner surface of the first and second lumens, and to secure the first and second PD catheter portions. The connector body may define a connector lumen configured to fluidically connect the first lumen of the first PD catheter portion and the second lumen of the second PD catheter portion. In some examples, the user may determine modify the length of the first or second PD catheter portion such that the connector is located at one of the first or second cuff positions, e.g., such that one of Ld or Lp is zero. For example, the connector may comprise a cuff, such as a fabric cuff (e.g., a Dacron™ cuff), a bead cuff, a disc cuff, a bead-and-flange cuff, or any suitable cuff. The user may modify the length of one of the first or second PD catheter portion at (506) and insert the connector-and-cuff at (508) such that the connector connects the first and second PD catheter portions at the first cuff position or the second cuff position.

Various examples of the disclosure have been described. Any combination of the described systems, operations, or functions is contemplated. These and other examples are within the scope of the following claims.

What is claimed is:

1. A catheter assembly comprising:
a first catheter body portion defining a first lumen and a plurality of sidewall openings open to the first lumen and configured to at least one of introduce fluid into a patient or remove fluid from the patient,
wherein at least a distal portion of the first catheter body portion is coiled;
a second catheter body portion defining a second lumen;
a first cuff proximal to a distal end of the first catheter body portion;
a second cuff distal to a proximal end of the second catheter body portion; and
a connector configured to mechanically connect the first and second catheter body portions between the first and second cuffs and to fluidically connect the first and second lumens,
wherein a distance between the first and second cuffs is modifiable by at least modifying one of a length of the first catheter body portion or a length of the second catheter body portion.

2. The catheter assembly of claim 1, wherein at least one of the first catheter body portion or the second catheter body portion comprises one or more markings along a length of the respective catheter body portion, wherein the one or more markings indicate a plurality of different catheter body portion lengths.

3. A catheter assembly comprising:
a first catheter body portion defining a first lumen and a plurality of sidewall openings open to the first lumen and configured to at least one of introduce fluid into a patient or remove fluid from the patient,
a second catheter body portion defining a second lumen;
a first cuff proximal to a distal end of the first catheter body portion;
a second cuff distal to a proximal end of the second catheter body portion; and
a connector configured to mechanically connect the first and second catheter body portions between the first and second cuffs and to fluidically connect the first and second lumens,
wherein a distance between the first and second cuffs is modifiable by at least modifying one of a length of the first catheter body portion or a length of the second catheter body portion, and
wherein the distance between the first and second cuffs is based on a determined length between a subcutaneous cuff position and a deep cuff position of the patient and based on a determined length between a pelvic gutter and the deep cuff position of the patient.

4. The catheter assembly of claim 3, wherein the deep cuff position is based on an internal peritoneal cavity entry site of the patient and the subcutaneous cuff position is based on an external exit site of the patient.

5. The catheter assembly of claim 1, wherein the connector comprises one of the first cuff or the second cuff.

6. The catheter assembly of claim 5, wherein the one of the first cuff or the second cuff comprises at least one of a bead cuff or a disc cuff.

7. The catheter assembly of claim 1, wherein the connector comprises a body and a plurality of barbs extending from the body.

8. The catheter assembly of claim 1, wherein the connector is configured to be received in the first and second lumens to connect the first and second catheter body portions.

9. The catheter assembly of claim 8, wherein when the connector is received in the first and second lumens and connects the first and second catheter body portions, at least part of the connector remains exposed.

10. The catheter assembly of claim 1, wherein the connector is configured to be positioned external to the first and second catheter body portions to connect the first and second catheter body portions.

11. A catheter assembly comprising:
a first catheter body portion defining a first lumen and a plurality of sidewall openings open to the first lumen and configured to at least one of introduce fluid into a patient or remove fluid from the patient, wherein the first catheter body portion includes a first cuff and one or more markings along its length;
a second catheter body portion defining a second lumen and comprising a second cuff and one or more markings along its length; and
a connector configured to be received in the first and second lumens to mechanically connect the first and second catheter body portions between the first and second cuffs and to fluidically connect the first and second lumens,
wherein a distance between first and second cuffs is modifiable by at least modifying one of a length of the first catheter body portion or a length of the second catheter body portion.

12. The catheter assembly of claim 11, wherein the distance between the first and second cuffs is based on a determined length between a subcutaneous cuff position and a deep cuff position of the patient and based on a determined length between a pelvic gutter and the deep cuff position of the patient.

13. The catheter assembly of claim 11, wherein the connector is configured to be received in the first and second lumens to connect the first and second catheter body portions.

14. The catheter assembly of claim 13, wherein when the connector is received in the first and second lumens and connects the first and second catheter body portions, at least part of the connector remains exposed.

15. The catheter assembly of claim 13, wherein the connector comprises a body and a plurality of barbs extending from the body, the plurality of barbs being configured to engage at least an inner surface of the first and second catheter body portions to secure the connector to the first and second catheter body portions.

16. The catheter assembly of claim 11, wherein the connector is configured to be positioned external to the first and second catheter body portions to connect the first and second catheter body portions.

17. A method of forming a peritoneal dialysis (PD) catheter, the method comprising: determining a first cuff position on a first catheter body portion;
determining a second cuff position on a second catheter body portion;
modifying at least one of a length of the first catheter body portion or a length of the second catheter body portion based on the first cuff position and the second cuff position; and
connecting, via a connector, the first catheter body portion and the second catheter body portion between the first cuff position and the second cuff position, wherein connecting the first and second catheter body portions comprises fluidically connecting a first lumen defined by the first catheter body portion and a second lumen defined by the second catheter body portion.

18. The method of claim 17, wherein the connector comprises a body and a plurality of barbs extending radially outwards from the body.

19. The method of claim 17, wherein the first cuff position is an internal peritoneal cavity entry site of the patient, wherein the first catheter body portion further comprises a deep cuff at the first cuff position, wherein the connector further comprises the deep cuff.

* * * * *